US011521724B2

(12) United States Patent
Das et al.

(10) Patent No.: US 11,521,724 B2
(45) Date of Patent: Dec. 6, 2022

(54) PERSONALIZED PATIENT ENGAGEMENT IN CARE MANAGEMENT USING EXPLAINABLE BEHAVIORAL PHENOTYPES

(71) Applicant: International Business Machines Corporation, Armonk, NY (US)

(72) Inventors: Subhro Das, Cambridge, MA (US); Gema Almoguera, Irving, TX (US); Kenneth J. Barker, Mahopac, NY (US); Ching-Hua Chen, New York, NY (US); Adam R. Faulkner, New York, NY (US); Pei-Yun Hsueh, New York, NY (US); Chandramouli Maduri, Elmsford, NY (US); Sara Rosenthal, Spring Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 236 days.

(21) Appl. No.: 16/593,178

(22) Filed: Oct. 4, 2019

(65) Prior Publication Data

US 2021/0104307 A1 Apr. 8, 2021

(51) Int. Cl.
*G16H 20/00* (2018.01)
*G16H 50/20* (2018.01)
(Continued)

(52) U.S. Cl.
CPC ......... *G16H 20/00* (2018.01); *G06K 9/00523* (2013.01); *G06N 5/04* (2013.01);
(Continued)

(58) Field of Classification Search
CPC ....... G06K 1/00–2221/2153; G06K 2215/111; G16H 10/00–80/00; G06N 3/00–99/007
See application file for complete search history.

(56) References Cited

U.S. PATENT DOCUMENTS 5,657,256 A 8/1997 Swnson et al.
6,039,688 A 3/2000 Douglas et al.
(Continued)

FOREIGN PATENT DOCUMENTS

CN 105912881 A 8/2016
WO WO2004/061744 A2 7/2004
(Continued)

OTHER PUBLICATIONS

Kohn et al., "IBM's Health Analytics and Clinical Decision Support," IMIA Yearbook of Medical Informatics, 2014: 154-162. (Year: 2014).*
(Continued)

*Primary Examiner* — Jonathon A. Szumny
(74) *Attorney, Agent, or Firm* — Stephen J. Walder, Jr.; Kristofer Haggerty

(57) ABSTRACT

A mechanism is provided in a data processing system to implement a personalized patient engagement engine. The personalized patient engagement engine develops a set of models for a plurality of behavioral phenotypes based on anonymized unstructured and structured patient-care management records for a plurality of patients over a period of time; matches a given patient to a behavioral phenotype; estimates a propensity of positive and/or negative behavioral responses of each of a plurality of targeted behaviors; dynamically updates personalized intervention effectiveness rankings in context for care manager and patient decision-making based on what has been shown to lead to positive responses for individuals with a similar behavioral profile; generates an intervention recommendation for the given patient based on the personalized intervention effectiveness rankings relative to the patient given an assigned goal and an individual intervention effect estimation; and provides the intervention recommendation to the care manager.

20 Claims, 7 Drawing Sheets

(51) Int. Cl.
*G16H 50/50* (2018.01)
*G06N 5/04* (2006.01)
*G16H 10/60* (2018.01)
*G06K 9/00* (2022.01)
*G16H 80/00* (2018.01)

(52) U.S. Cl.
CPC ............ *G16H 10/60* (2018.01); *G16H 50/20* (2018.01); *G16H 50/50* (2018.01); *G16H 80/00* (2018.01)

(56) References Cited

U.S. PATENT DOCUMENTS

| | | | |
|---|---|---|---|
| 6,802,810 | B2 | 10/2004 | Ciarniello et al. |
| 6,915,254 | B1 | 7/2005 | Heinze et al. |
| 7,001,334 | B2 | 2/2006 | Reed et al. |
| 7,165,012 | B2 | 1/2007 | Swanson |
| 8,109,874 | B2 | 2/2012 | Kong et al. |
| 8,566,121 | B2 | 10/2013 | Ramasubramanian et al. |
| 8,706,731 | B2 | 4/2014 | Cho et al. |
| 10,109,377 | B2 | 10/2018 | Shetty et al. |
| 2006/0150989 | A1 | 7/2006 | Migaly |
| 2007/0219059 | A1 | 9/2007 | Schwartz et al. |
| 2008/0154693 | A1 | 6/2008 | Bateni et al. |
| 2008/0268412 | A1 | 10/2008 | Mulcahy et al. |
| 2008/0312959 | A1 | 12/2008 | Rose et al. |
| 2009/0182580 | A1 | 7/2009 | Martin et al. |
| 2010/0076786 | A1* | 3/2010 | Dalton .................. G16H 10/60 705/3 |
| 2011/0301977 | A1 | 12/2011 | Belcher et al. |
| 2012/0129139 | A1 | 5/2012 | Partovi |
| 2012/0316891 | A1* | 12/2012 | Friedlander ............ G06F 19/00 705/2 |
| 2014/0052475 | A1* | 2/2014 | Madan .................. G16H 50/50 705/3 |
| 2014/0214441 | A1 | 7/2014 | Young et al. |
| 2014/0244292 | A1* | 8/2014 | Rosenberg ............ G16H 70/00 705/2 |
| 2014/0310016 | A1* | 10/2014 | Kenney .................. G16H 50/70 705/2 |
| 2015/0019259 | A1 | 1/2015 | Qureshi et al. |
| 2015/0178811 | A1 | 6/2015 | Chen |
| 2015/0286784 | A1* | 10/2015 | Hagigi .................. G16H 50/20 705/2 |
| 2015/0363569 | A1 | 12/2015 | Ryan et al. |
| 2016/0106627 | A1 | 4/2016 | Geman et al. |
| 2016/0147976 | A1 | 5/2016 | Jain et al. |
| 2016/0171177 | A1* | 6/2016 | Caffarel .................. G06Q 40/08 705/3 |
| 2016/0180228 | A1 | 6/2016 | Ozbay |
| 2016/0224762 | A1 | 8/2016 | Gibson et al. |
| 2016/0321413 | A1 | 11/2016 | Cheyne |
| 2017/0004260 | A1* | 1/2017 | Moturu .................. G16H 50/20 |
| 2017/0004402 | A1* | 1/2017 | Graham ............... G06F 16/9535 |
| 2017/0235912 | A1* | 8/2017 | Moturu .................. G16H 50/50 705/2 |
| 2017/0329917 | A1* | 11/2017 | McRaith ................ G16H 40/67 |
| 2018/0082030 | A1* | 3/2018 | Allen ..................... G16H 70/20 |
| 2018/0144820 | A1 | 5/2018 | Grimmer et al. |
| 2018/0300640 | A1* | 10/2018 | Birnbaum ............. G16H 10/60 |
| 2019/0013088 | A1 | 1/2019 | Moturu et al. |
| 2019/0385259 | A1* | 12/2019 | Tayal ..................... G06Q 30/02 |
| 2020/0005939 | A1* | 1/2020 | Stevens ................. G16H 20/30 |
| 2021/0057107 | A1* | 2/2021 | Solomon ............... G16H 50/50 |
| 2021/0098135 | A1* | 4/2021 | Frings ................... G06N 7/005 |

FOREIGN PATENT DOCUMENTS

| | | | |
|---|---|---|---|
| WO | WO2005/081119 | A2 | 9/2005 |
| WO | WO2006/026641 | A1 | 3/2006 |
| WO | WO2008/060854 | A2 | 5/2008 |
| WO | WO2011/103346 | A1 | 8/2011 |
| WO | WO2011/103495 | A3 | 8/2011 |
| WO | WO2016/187374 | A1 | 11/2016 |
| WO | WO2017/095796 | A1 | 8/2017 |
| WO | WO-2018200877 | A1 * | 11/2018 ............ G16H 10/20 |
| WO | WO-2019018580 | A1 * | 1/2019 ............ C12Q 1/68 |
| WO | WO-2019073081 | A * | 4/2019 ............ G16H 80/00 |
| WO | WO-2020234388 | A1 * | 11/2020 ............ G16H 10/20 |

OTHER PUBLICATIONS

Katzman et al., "DeepSurv: personalized treatment recommender system using a Cox proportional hazards deep neural network," BMC Medical Research Methodology, (2018) 18:24, pp. 1-12. (Year: 2018).*

Deng, Yihan et al., "Retrieving Attitudes: Sentiment Analysis from Clinical Narratives", MedI R Jul. 11, 2014, Gold Coast, Australia, 4 Pages.

Ghassemi, Mohammad M. et al., "A Visualization of Evolving Clinical Sentiment Using Vector Representations of Clinical Notes", Computing in Cardiology Conference, Sep. 6-9, 2015, Nice, France, pp. 629-632.

Hazlehurst PHD., Brian et al., "MediClass: A System for Detecting and Classifying Encounter-Based Clinical Events in any electronic Medical Record", Journal of the American Medical Informatics Association, vol. 12, No. 5, Sep./Oct. 2005, pp. 517-529.

Mishra MD. MS., Ninad K. et al., "Towards Automatic Diabetes Case Detection and ABCS Protocol Compliance Assessment", Clinical Medicine and Research, Feb. 2012, vol. 10, No. #, pp. 106-121.

Topaz, Maxim et al., "Studying Associations Between Heart Failure Self-Management and Rehospitalizations Using Natural Language Processing", 2017 Western Journal of Nursing Research, Downloaded from the wjn.sagepub.com at University of Haifa Library on Sep. 21, 2016, pp. 1-19.

\* cited by examiner

PERSONALIZED PATIENT ENGAGEMENT IN CARE MANAGEMENT USING EXPLAINABLE BEHAVIORAL PHENOTYPES

BACKGROUND

The present application relates generally to an improved data processing apparatus and method and more specifically to mechanisms for personalized patient engagement in care management using explainable behavioral phenotypes.

An electronic health record (EHR) or electronic medical record (EMR) or care management record (CMR) is the systematized collection of patient and population electronically stored health information in a digital format. These records can be shared across different health care settings. Records are shared through network-connected, enterprise-wide information systems or other information networks and exchanges. EMRs and CMRs may include a range of data, including demographics, social history, medical history, medication and allergies, immunization status, laboratory test results, radiology images, vital signs, personal statistics like age and weight, and billing information.

A computerized healthcare cognitive system may be configured to assist patient care management based on CMR and/or EMR data for patients. The healthcare cognitive system may be directed to assist a care manager in treating a plurality of patients based on reported symptoms and other information gathered about the patients. The healthcare cognitive system may operate on requests and patient attributes utilizing information gathered from a medical corpus and other source data, treatment guidance data, patient CMRs and EMRs associated with the patients to assist with patient care management.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a personalized patient engagement engine. The method comprises developing, by the personalized patient engagement engine, a set of models for a plurality of behavioral phenotypes based on anonymized unstructured care management notes and anonymized structured patient-care management records for a plurality of patients over a period of time. The method further comprises matching, by the personalized patient engagement engine, a given patient to a behavioral phenotype based on the set of models and estimating, by the personalized patient engagement engine, a propensity of positive behavioral responses of each of a plurality of targeted behaviors. The method further comprises dynamically updating, by the personalized patient engagement engine, personalized intervention effectiveness rankings in context for care manager and patient decision-making based on what has been shown to lead to positive responses for individuals with a similar behavioral profile. The method further comprises generating, by the personalized patient engagement engine, an intervention recommendation for the given patient based on the personalized intervention effectiveness rankings relative to the patient given an assigned goal and an individual intervention effect estimation and providing, by the personalized patient engagement engine, the intervention recommendation to the care manager.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
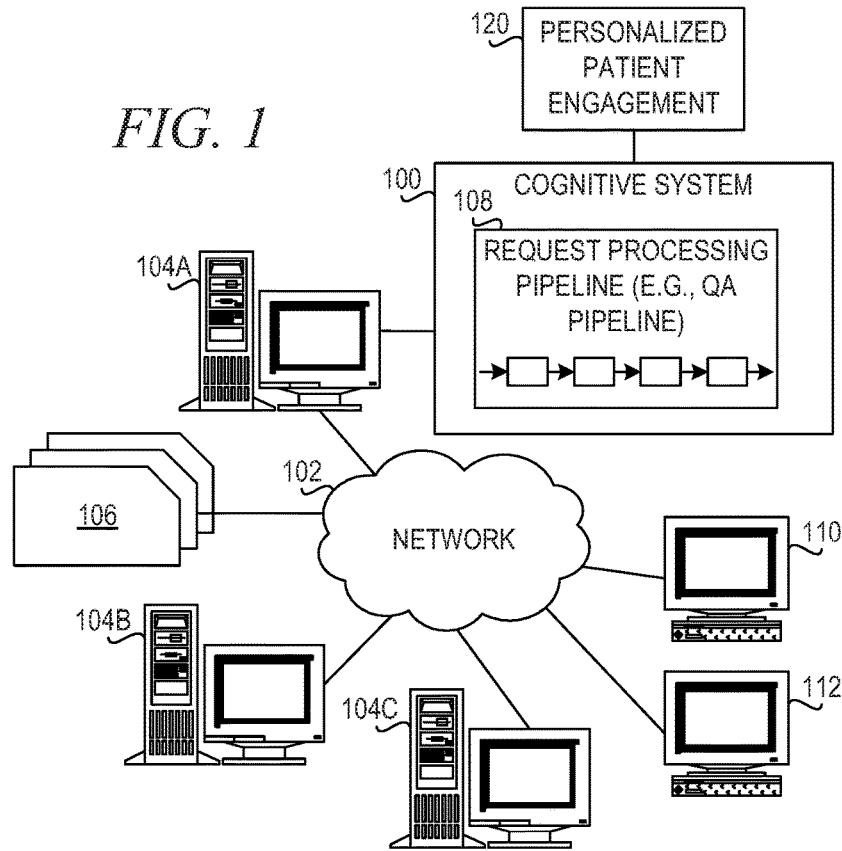
FIG. 1 depicts a schematic diagram of one illustrative embodiment of a cognitive healthcare system in a computer network.

Recent studies have documented the importance of individuality and heterogeneity in care planning. Yet today's care programs are still structured around population-level evidence. In practice, varying behavioral responses are revealed in patients' care management (CM) records. With current care programs, care managers cannot take advantage of such individual-level patient engagement cues and adjust intervention for improved effectiveness for personalized care. CMs monitor patient engagement, identify self-management goals, record notes, and provide recommendations. CMs report their recommendations in CM notes and may or may not describe the patient's engagement with respect to the recommendation using inconsistent reporting practices. Interventions and goals for the patients from a pre-defined list that is general.

There is currently no existing indicator of patient engagement level for the care manager. CMs rely on browsing previous notes to identify patient engagement with respect to medication guidelines, post-operation regimens, and physician-recommended changes in health behavior. As a manual process, it is hard for the CM to efficiently analyze the notes. It is very difficult for the CM to assign a behavioral profile to the patient based on other similar patients. There are signals in how the CM responds to the engagement (e.g., whether to call a patient, whether to take on a particular intervention) that are completely lost in current systems.

The illustrative embodiments provide a system that can assess not only population-level evidence but subgroup-level evidence and personal-level evidence. In particular, the system can learn on the fly, classifying behavioral response from both the structured and unstructured CM records to inform individual-level intervention decisions exceeding human ability to provide optimal care. The illustrative embodiments provide a care management computer system that dynamically recommends interventions and goals for a patient at the personal level, using population, subgroup-level, and individual-level evidence collectively. The care management computer system provides a quantitative representation of engagement personalized towards generated behavioral phenotypes that is explainable.

The illustrative embodiment helps with summarizing a large number of confounders of patient engagement behaviors into a single score for easy interpretation. The CM system of the illustrative embodiment identifies differential patient engagement strategies by observing revealed patient behavioral response of the target behaviors in different behavioral profiles. The CM system also discovers best practices based on the interpretable behavioral profiles by quantifying the effectiveness of interventions within different behavioral profiles.

The illustrative embodiment automatically identifies CM recommendations and evidence of patient engagement/non-engagement. The CM system of the illustrative embodiment assesses CM effectiveness by learning globally at the population level and identifies the behavioral profile of the patients based on the notes and structured data. The CM system provides new personalized recommendations and goals dynamically using contextual information and information regarding relevant public health problems.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
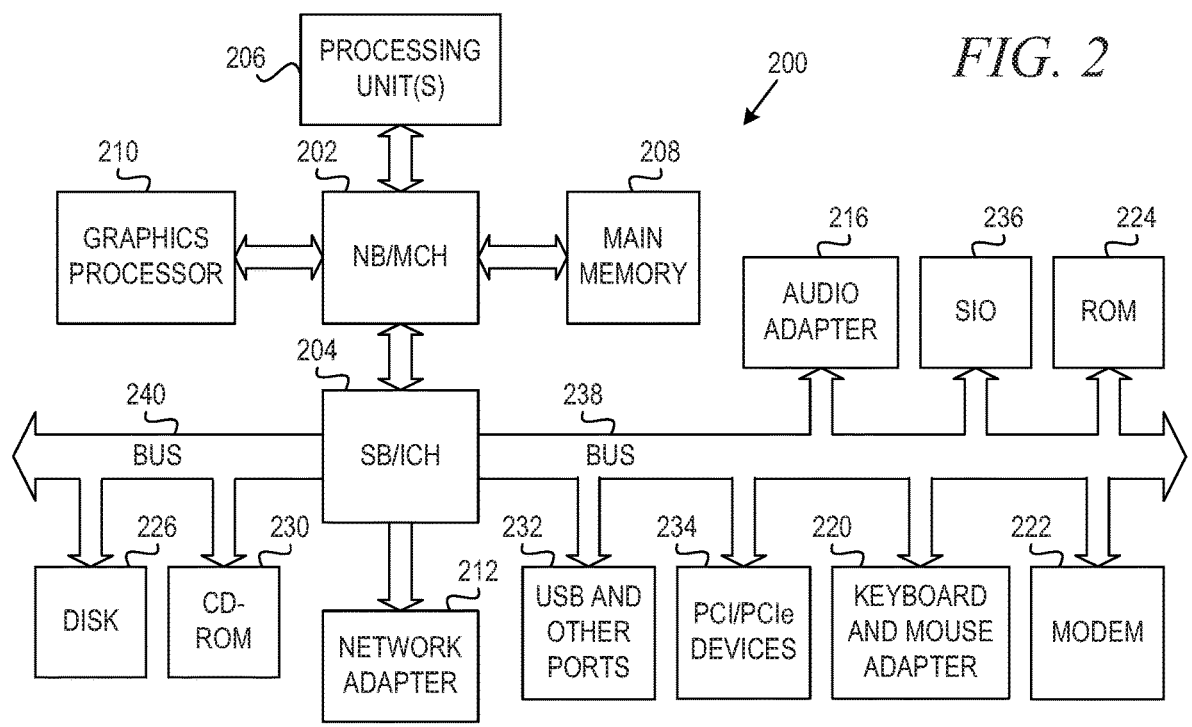
FIG. 2 is a block diagram of an example data processing system in which aspects of the illustrative embodiments are implemented.
Figure 3:
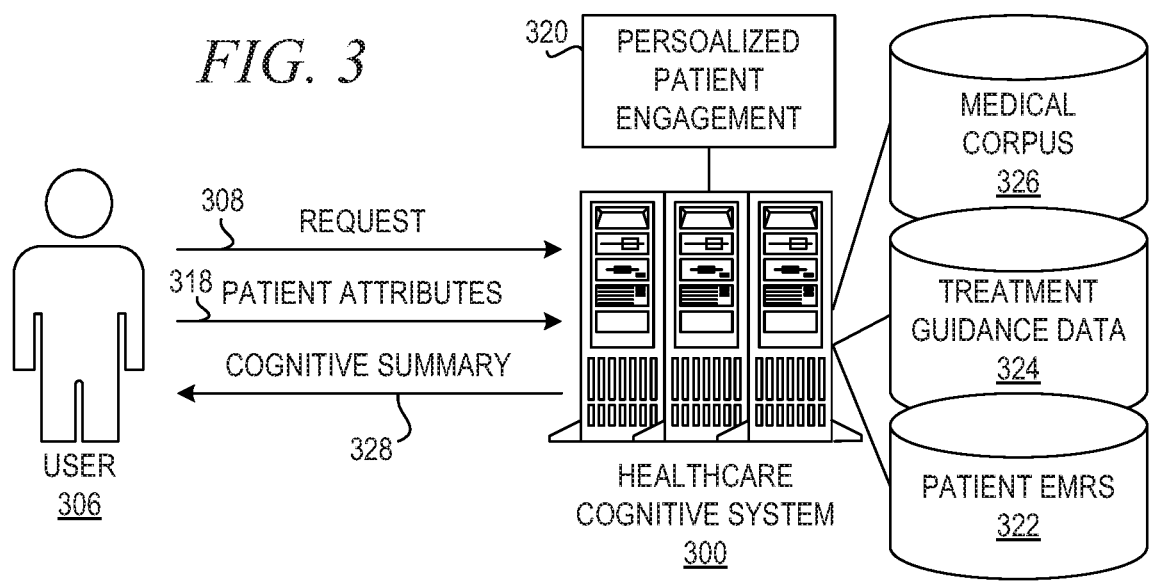
FIG. 3 is an example diagram illustrating an interaction of elements of a healthcare cognitive system in accordance with one illustrative embodiment.

As noted above, the present invention provides mechanisms for graphical presentation of relevant information from electronic medical records. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for personalized patient engagement in care management using explainable behavioral phenotypes.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. These corpora may include, but are not limited to, EMR data. The cognitive system may evaluate intervention effectiveness (e.g., goal attained or not) to quantify varying patient responses to the same intervention, identify patient behavioral profile (e.g., middle-aged patients require more nudges to get positive response to referral), identify patient engagement/non-engagement cues (e.g., patient adherence to medication guidelines, post-operation regimens, physician-recommended changes in health behavior, patient admits to cheating on diet), and monitor outcomes of recent intervention recommendation (e.g., post-education adherence).

As will be discussed in greater detail hereafter, the illustrative embodiments may be integrated in, augment, and extend the functionality of these request processing pipeline mechanisms of a healthcare cognitive system with regard to personalized patient engagement.

Thus, it is important to first have an understanding of how cognitive systems are implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing an input request based on information obtained from the corpus or corpora of data 106. The pipeline 108 generates responses for the input question or request based on the processing of the input request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate responses to generate ranked listing of candidate responses, which may then be presented to the user that submitted the input request, e.g., a user of client computing device 110, or from which a final response is selected and presented to the user.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare-based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a personalized patient engagement engine 120 for finding a specific configuration of a care plan dynamically at the personal level, using population, subgroup-level, and individual-level evidence collectively.

Personalized patient engagement engine 120 improves performance of care plan personalization given the increased patient understanding and care manager (CM) work productivity, enabling learning with reduced bias based on practice-based evidence. Personalized patient engagement engine 120 is operative based on evidence that has been or can be collected by providers in a health network. Personalized patient engagement engine 120 receives as input program referrals for patients from physicians, care manager (CM) updates on patients' program/goal/intervention records, and CM-patient communication history, including calls, email logs, etc.

Personalized patient engagement engine 120 processes both structured and unstructured data and generates automatic features. Personalized patient engagement engine 120 extracts patient engagement semantics from CM notes using natural language processing (NLP) tools. Personalized patient engagement engine 120 trains a feature transformation operator using supervised metric learning and creates separate modules for automatically learned behavioral segments. For each module, personalized patient engagement engine 120 trains regressors (generalized learning model (GLM)) and estimators and stores the model parameters.

In addition to a patient summary, personalized patient engagement engine 120 outputs surface recommendations to CMs on patient's likelihood of program enrollment/completion and goal attainment and predicted effectiveness of different interventions on the patient. Personalized patient engagement engine 120 also retrieves from the CM annotations of dynamically selected entities for model correction.

Personalized patient engagement engine 120 provides interoperability with shared decision making with a closed loop human-machine system. Personalized patient engagement engine 120 provides confidence levels of predictive recommendations for patient engagement. Personalized patient engagement engine 120 obtains most important features from structured data and phrases from unstructured notes and derives evidence based on prototypical patients similar to the current case.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide personal patient engagement in care management using explainable behavioral phenotypes. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to assist the user 306 in providing care plans at the personal level, using population, subgroup-level, and individual-level evidence with reduced bias based on practice-based evidence. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. The cognitive summary 328 may be presented in a ranked ordering with associated supporting evidence, obtained from the patient attributes 318 and data sources 322-326, indicating the reasoning as to why the care plan is being provided.

Note that EMR data 322 or data presented to the user may come from home readings or measurements that the patient makes available and are collected into EMR data 322.

In accordance with the illustrative embodiments herein, the healthcare cognitive system 300 is augmented to include a personalized patient engagement engine 320 for providing care plans at the personal level, using population, subgroup-level, and individual-level evidence with reduced bias based on practice-based evidence. Engagement refers to patient self-monitoring of lifestyle choices, goal adoption, and the enlistment of self-efficacy beliefs. Adherence refers to patients following provider goals and advice. Engagement-bearing language can include adherence-bearing language (e.g., "patient is monitoring blood sugar, made follow-up appointment"). However, in addition, engagement-bearing language can include mentions of social ties (e.g., "discusses struggles to lose weight with sister") and positive or negative evaluations of health-related goals (e.g., "patient was irritable when asked about efforts to reduce smoking"). Neither of these involve adherence. Behavioral phenotype refers to the characteristics of a cohort of patients who are similar in terms of interactional, contextual, and behavioral features driving differential engagement outcomes.

Figure 4:
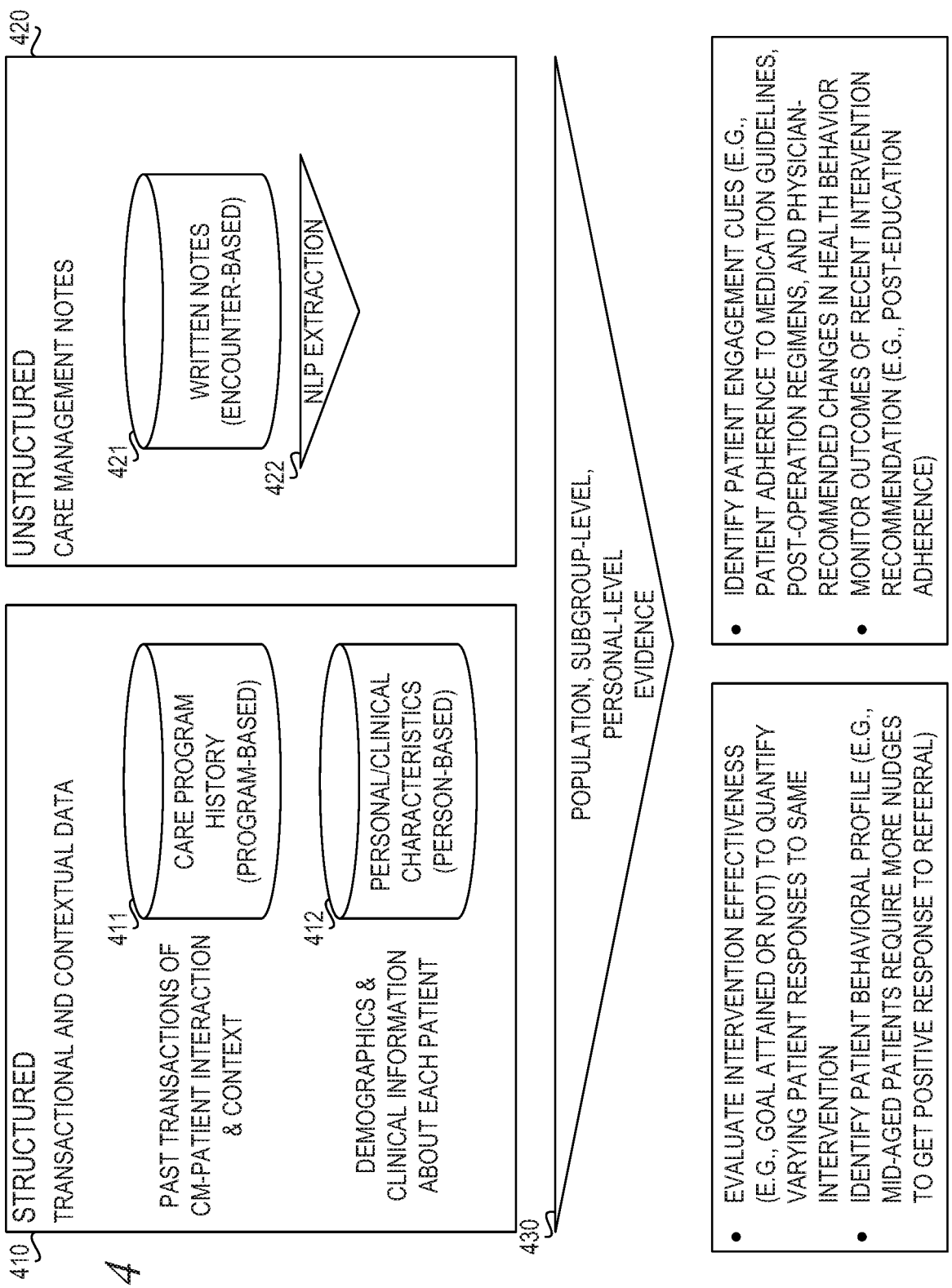
FIG. 4 illustrates a care management system in accordance with an illustrative embodiment.

FIG. 4 illustrates a care management system in accordance with an illustrative embodiment. Existing CM systems are population based, which has its limitations. Existing systems do not account for individuality and heterogeneity in care planning. However, there exist engagement cues in both structured data and unstructured data sources in a CM system.

Structured data 410 include transactional and contextual data. Care program history data 411 are program-based and include past transactions of CM-patient interaction and context. Personal/clinical characteristics data 412 are person-based and include demographic and clinical information about each patient.

Unstructured data 420 include care management notes. Written notes 421 are encounter-based. Natural language processing (NLP) extraction 422 is performed to extract features from the unstructured data 420, including written notes 421.

The CM system of the illustrative embodiment extracts population, subgroup-level, and personal-level evidence in block 430. The CM system evaluates intervention effectiveness (e.g., goal attained or not) to quantify varying patient responses to the same intervention. The CM system identifies patient behavioral profile (e.g., middle-aged patients require more nudges to get positive response to referral). The CM system identifies patient engagement cues (e.g., patient adherence to medication guidelines, post-operation regimens, and physician-recommended changes in health behavior. The CM system also monitors outcomes of recent intervention recommendation (e.g., post-education adherence).

Learning different levels of evidence from practice directly enables a new class of interesting use cases. For example, a first example use case is as an engagement assistant at referral and before each touch point. The illustrative embodiment improves care manager work productivity via identifying influenceable patients. That is, the CM system of the illustrative embodiment decides whom to engage. The care manager may ask the system to show the top ten patients to work on today for enrolling in a chronic care program with high clinical risk and high propensity to behaviorally respond to program enrollment call and previous enrollment history of Transition Care Program.

Another use case is as a care plan personalization assistant in ongoing care. The CM system recommends patient-specific goals (e.g., weight loss) and corresponding interventions for achieving those goals (e.g., self-monitoring, counseling).

Yet another use case is best practice learning. The CM system provides an explainable assessment of the practice patterns of CMs that lead to desirable patient outcomes. These patterns can be candidates for "best practice" behaviors that CMs are encouraged to adopt more systemically and systematically.

Another use case is where the CM system replaces the care manager role with a chat bot. The CM system provides the chat bot with the dialog to be used in a virtual conversation with the patient. The user interface of the chat bot may be via a visual display on a wearable device (e.g., a fitness band or smartwatch). It may also be via artificial voice/auditory communication on a wearable device or other non-wearable device (e.g., smart speaker). The chat bot converses with the patient using the dialog provided by the CM system. The chat bot records the conversation, which is stored in the CM system and is accessible to a human care manager through a separate interface created for the human care manager.

Figure 5:
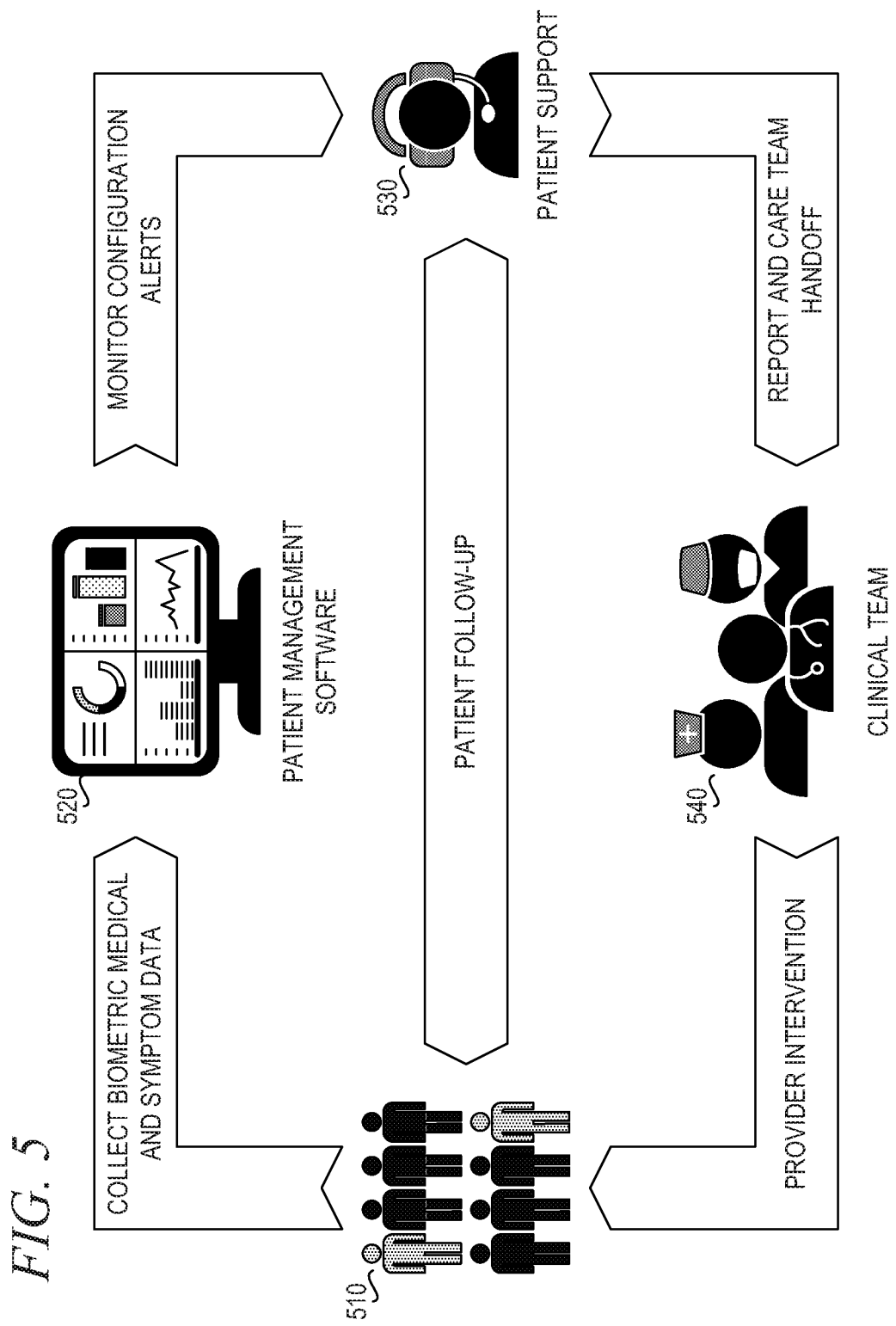
FIG. 5 illustrates a care management overview in accordance with an illustrative embodiment.

FIG. 5 illustrates a care management overview in accordance with an illustrative embodiment. Patient management software 520 collects biometric medical and symptom data from patients 510. Patient support personnel 530 monitor configuration alerts from patient management software 520. Based on the configuration alerts, patient support personnel 530 perform patient follow-up with patients 510 and perform reporting and care team handoff to clinical team 540, which then performs provider intervention with patients 510.

Figure 6:
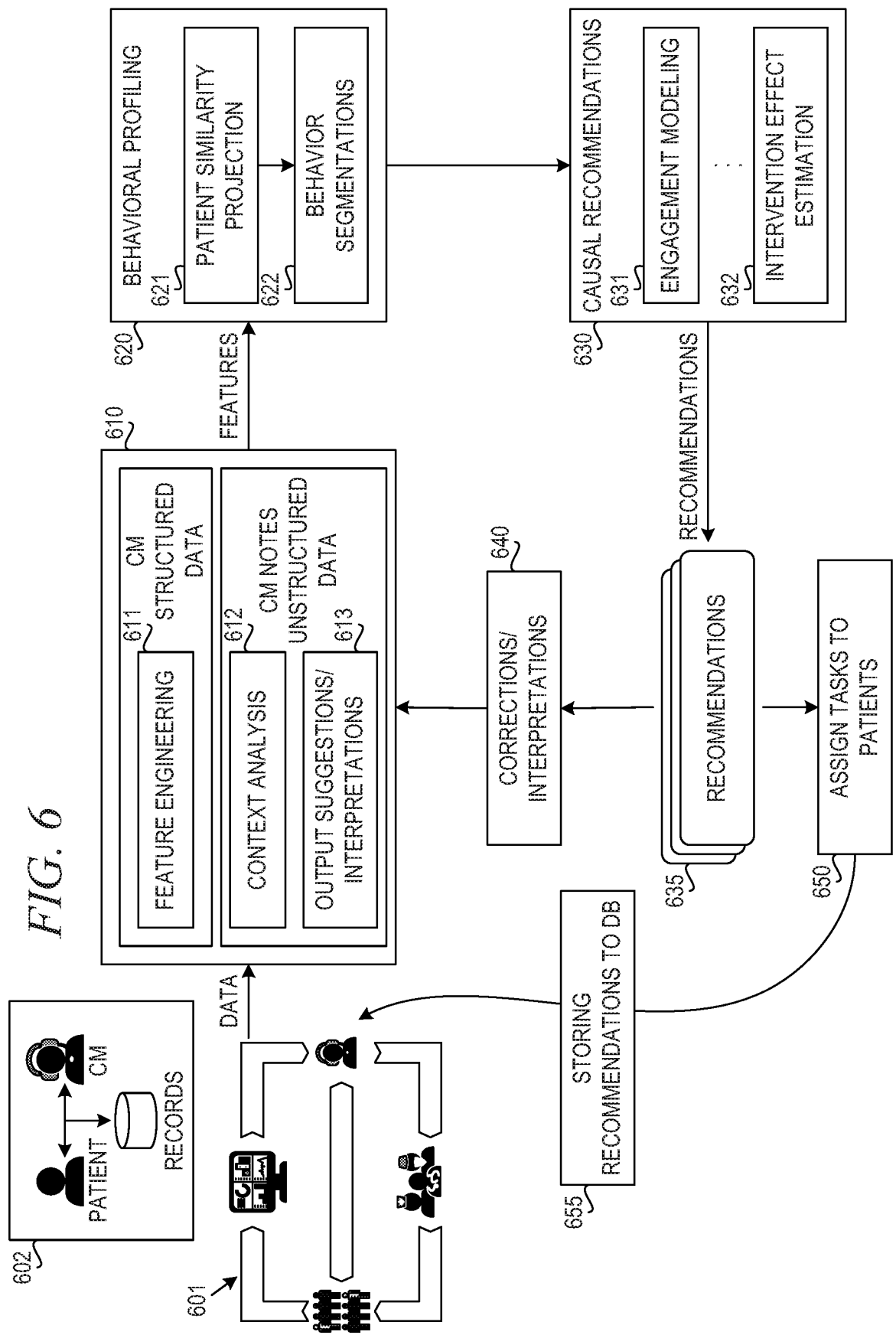
FIG. 6 is a block diagram of a system for personalized patient engagement in care management using explainable behavioral phenotypes in accordance with an illustrative embodiment.

FIG. 6 is a block diagram of a system for personalized patient engagement in care management using explainable behavioral phenotypes in accordance with an illustrative embodiment. The care management process 601 provides data to care management (CM) data extraction 610, which includes CM structured data extraction and CM unstructured data extraction. Care management process 601 includes communication between a patient and a care manager with records being stored in record storage in block 602.

CM structured data extraction includes feature engineering 611. CM unstructured data extraction includes context analysis 612 and output suggestions and interpretations 613. CM data extraction 610 provides features to behavioral profiling 620. In the depicted example, behavioral profiling 620 includes patient similarity projection 621 and behavior segmentations 622. Behavioral profiling 620 provides the segment identifier and centroid coordinates in the projected feature space and the behavioral segment membership of each patient to causal recommendations component 630.

Causal recommendations component 630 provides recommendations 635. Causal recommendations component 630 includes machine learning based causal inference pipelines, such as engagement modeling 631 and/or intervention effect estimation modeling 632. Using the engagement model of the illustrative embodiment, other machine learning based causal inference pipelines can be used to generate causal recommendations. Recommendations 635 may be used to assign tasks to patients in block 650 and to store the recommendation records back to the database in block 655. These tasks may include enrolling in institutional wellness programs, reading educational materials, adopting a new dietary pattern, for example. Recommendations 635 may also be used to provide corrections and/or interpretations 640 to CM data extraction 610.

Figure 7:
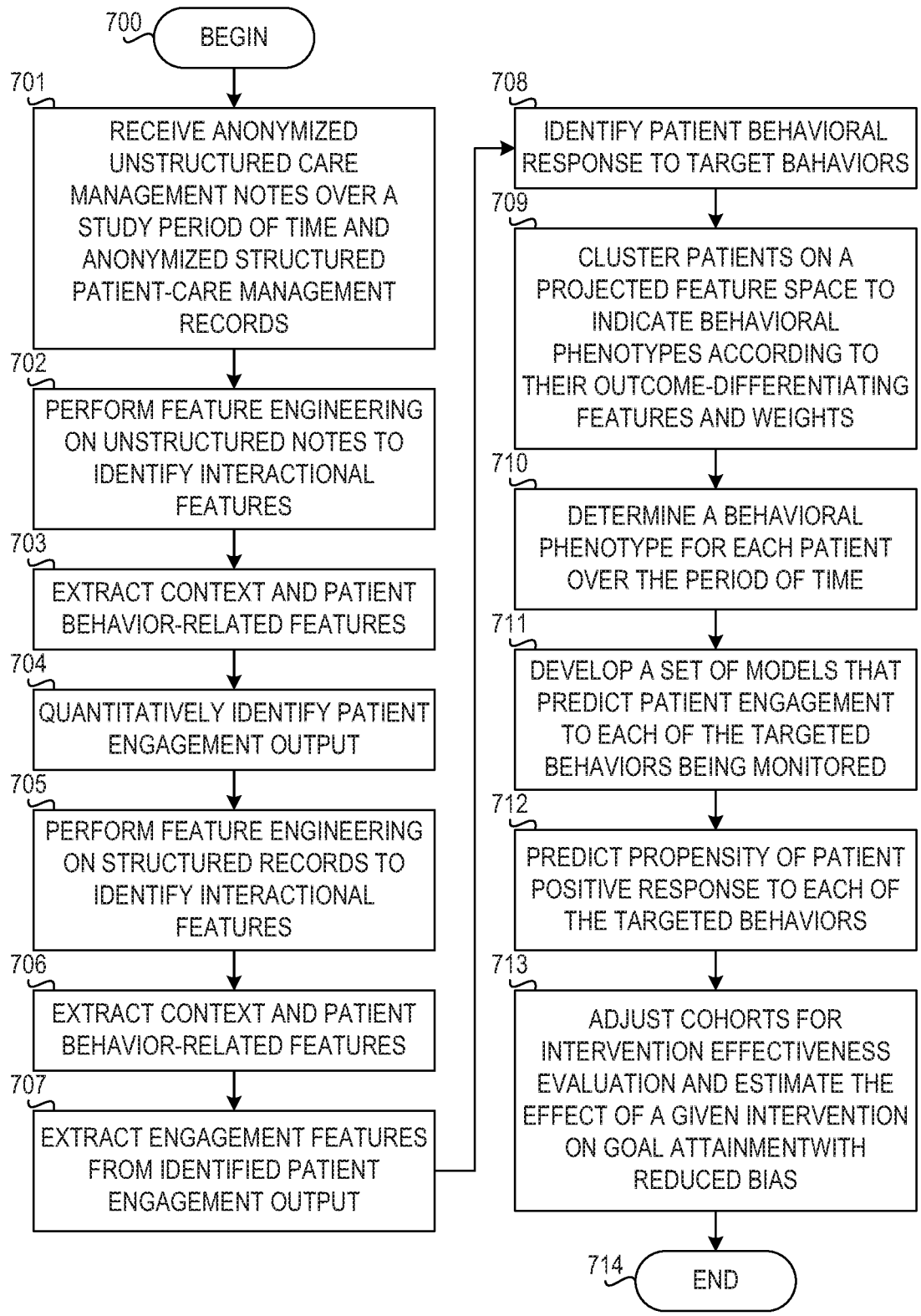
FIG. 7 is a flowchart illustrating operation of training a system for personalized patient engagement in care management in accordance with an illustrative embodiment.

FIG. 7 is a flowchart illustrating operation of training a system for personalized patient engagement in care management in accordance with an illustrative embodiment. Operation begins (block 700), and the mechanism receives anonymized unstructured care management notes over a study period of time and anonymized structured patient-care management records (block 701). The mechanism performs feature engineering on the unstructured notes to identify interactional features (block 702). The mechanism then extracts context and patient behavior-related features (block 703). Then, the mechanism quantitatively identifies patient engagement output (block 704).

Then, the mechanism performs feature engineering on structured records to identify interactional features (block 705). The mechanism extracts context and patient behavior-related features (block 706). The mechanism then extracts engagement features from the identified patient engagement output (block 707). The mechanism identifies patient behavioral response to target behaviors (e.g., program enrollment, self-management goal attainment, adherence to medication, etc.) (block 708). The mechanism clusters patients on a projected feature space to indicate behavioral phenotype according to their outcome-differentiating features and weights (block 709). The behavioral phenotypes are composed of a number of prototypical patient cases according to their interactional, contextual, and behavioral features over a period of time. Then, the mechanism determines behavioral phenotype for each patient over the period of time (block 710).

The mechanism develops a set of models that predict patient engagement to each of the targeted behaviors being monitored (block 711). The mechanism predicts propensity of patient positive response to each of the targeted behaviors (block 712). Based on the propensity to goal attainment and behavioral phenotypes, the mechanism adjusts the cohorts (clusters) for intervention effectiveness evaluation and estimate the effect of a given intervention on goal attainment with reduced bias (block 713). Thereafter, operation ends (block 714).

Figure 8:
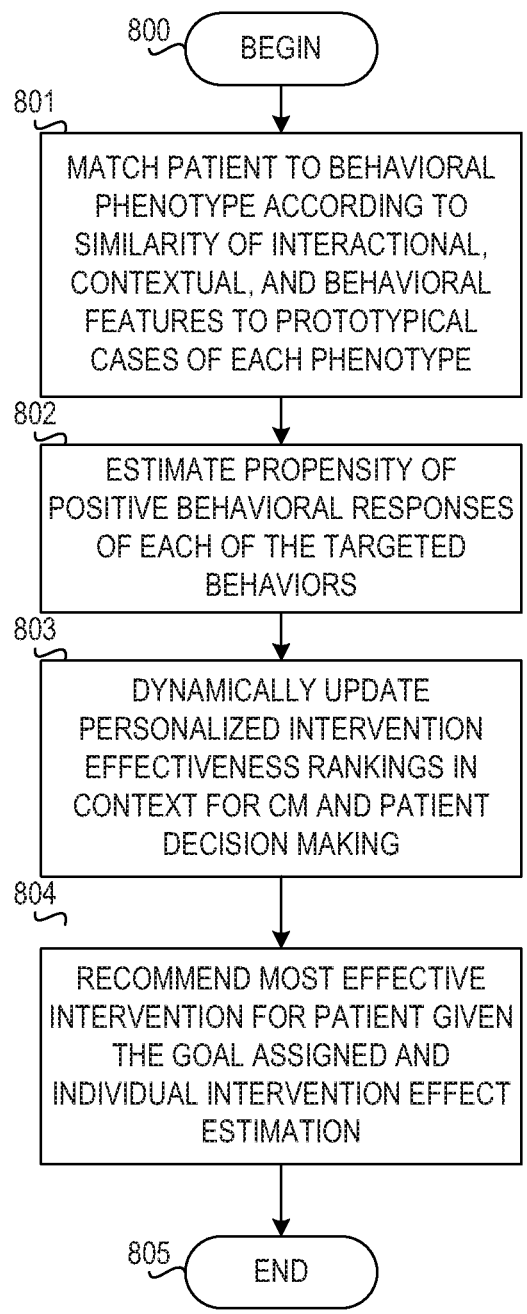
FIG. 8 is a flowchart illustrating operation of personalized patient engagement in care management using explainable behavioral phenotypes in accordance with an illustrative embodiment.

FIG. 8 is a flowchart illustrating operation of personalized patient engagement in care management using explainable behavioral phenotypes in accordance with an illustrative embodiment. Operation begins with a new unseen patient (block 800). The mechanism matches the patient to a behavioral phenotype according to a similarity of the patient's interactional, contextual, and behavioral features to the prototypical cases of each phenotype (block 801). The mechanism estimates the propensity of positive behavioral responses of each of the targeted behaviors (block 802). Then, the mechanism dynamically updates the personalized intervention effectiveness rankings in context for CM and patient's decision-making based on what has been shown to lead to positive responses for individuals with similar behavioral profile (block 803). Based on the ranking, the mechanism recommends the most effective intervention for the patient given the goal assigned and the individual intervention effect estimation (block 804). Thereafter, operation ends (block 805).

For example, when a new patient is newly diagnosed of Diabetes, this patient is referred to a chronic disease management program being supported by a care manager team with our system in the backend. The system will use the care management information and the care manager interaction history of this patient to understand how best to engage this patient to successfully obtain his/her health goal of being able to self-manage disease. For any two patients with similar conditions, it is still possible that the way they would like to be engaged would be drastically different. While one might prefer to receive coaching-type of interventions, the other one might prefer to just be given the education materials.

As another example, a patient may be assigned the goal of reducing their weight by a certain number of pounds over the next six months. In order to determine recommended intervention for this patient for meeting this goal, the system would first identify the behavioral phenotype to which this patient is most aligned. Based on the phenotypic alignment, the CM system would determine the propensity of the patient to engage any intervention for achieving the assigned goal. Additionally, the CM system would rank candidate interventions (e.g., attend four-sessions of in-person counseling sessions with a registered dietician, enroll in weight watchers, read educational material on health eating and exercising) for the current goal. The ranking is based on the combined effect of the intervention and the propensity of the patient to engage in the intervention, for the stated goal.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a personalized patient engagement engine, the method comprising:
   developing, by the personalized patient engagement engine, a set of machine learning trained computer models that predict patient engagement to each of a plurality of targeted behaviors, wherein patient engagement is patient self-monitoring of lifestyle choices, goal adoption, and enlistment of self-efficacy beliefs, based on patient engagement semantics in one or more electronic corpora of patient data, comprising anonymized unstructured care management notes and anonymized structured patient-care management records, for a plurality of patients over a period of time, wherein the one or more corpora of patient data comprises patient data, for a population of patients, obtained from computing systems of a provider in a health network, and wherein developing the set of machine learning trained computer models comprises:
      clustering patients on a projected feature space, based on outcome-differentiating features and weights, to generate a plurality of clusters, the clusters in the plurality of clusters being associated with corresponding behavioral phenotypes, to thereby generate subgroup level evidence data, wherein the behavioral phenotypes comprise characteristics of a cohort of patients who are similar in terms of interactional, contextual, and behavioral features driving differential patient engagement outcomes, and
      executing supervised machine learning operations on computer models based on input patient features extracted from the one or more corpora of patient data to train regressors and estimators of the computer models and store corresponding trained computer model parameters for configuring the computer models to generate the set of machine learning trained computer models, wherein each machine learning trained computer model operates on the input patient features to predict whether a corresponding patient, based on the input patient features, will have a positive response to a corresponding targeted behavior;
   matching, by the personalized patient engagement engine, based on new patient input data for a given patient, the given patient to a behavioral phenotype of the behavioral phenotypes, wherein the plurality of behavioral phenotypes are composed of a number of prototypical patient cases according to their interactional, contextual, and behavioral features over the period of time;
   executing, in the data processing system, the set of machine learning trained computer models on features extracted from the new patient input data to generate estimates of a propensity of positive behavioral responses of each of the plurality of targeted behaviors;
   dynamically updating, by the personalized patient engagement engine, personalized intervention effectiveness rankings based on what has been shown to lead to positive responses for individuals with a similar behavioral profile, based on a corresponding cluster in the plurality of clusters, the matched behavioral phenotype, and the generated estimates of the propensity of the positive behavioral responses;
   generating, by the personalized patient engagement engine, an intervention recommendation for the given patient based on the personalized intervention effectiveness rankings relative to the patient given an assigned goal and an individual intervention effect estimation of achieving the assigned goal; and
   providing, by the personalized patient engagement engine, the intervention recommendation to a care manager.

2. The method of claim 1, wherein developing the set of machine learning trained computer models comprises:
   performing feature engineering on the anonymized unstructured care management notes to identify interactional features;
   extracting context and patient behavior-related features from the anonymized unstructured care management notes; and quantitatively identifying patient engagement based on the extracted context and patient behavior-related features to form patient engagement output.

3. The method of claim 2, wherein developing the set of machine learning trained computer models further comprises:
performing feature engineering on the anonymized structured patient-care management records to identify interactional features;
extracting context and patient behavior-related features from the anonymized structured patient-care management records;
extracting engagement features from the patient engagement output; and
identifying patient behavioral responses to target behaviors.

4. The method of claim 3, wherein matching the given patient to a behavioral phenotype comprises matching the given patient according to similarity of the given patient's interactional, contextual, and behavioral features to the prototypical cases of each behavioral phenotype.

5. The method of claim 3, further comprising providing corrections and interpretations to the extracted engagement features.

6. The method of claim 1, further comprising:
assigning one or more tasks to the given patient based on the recommended intervention; and
storing recommendation records for the recommended intervention to a database.

7. The method of claim 1, further comprising using at least one machine learning based causal inference pipeline to generate causal recommendations, wherein the at least one machine learning based causal inference pipeline comprises engagement modeling or intervention effect estimation modeling.

8. A non-transitory computer program product comprising a computer readable storage medium having a computer readable program stored therein, wherein the computer readable program, when executed on a processor of a data processing system, causes the data processing system to implement a personalized patient engagement engine, wherein the computer readable program causes the data processing to:
develop, by the personalized patient engagement engine, a set of machine learning trained computer models that predict patient engagement to each of a plurality of targeted behaviors, wherein patient engagement is patient self-monitoring of lifestyle choices, goal adoption, and enlistment of self-efficacy beliefs, based on patient engagement semantics in one or more electronic corpora of patient data, comprising anonymized unstructured care management notes and anonymized structured patient-care management records, for a plurality of patients over a period of time, wherein the one or more corpora of patient data comprises patient data, for a population of patients, obtained from computing systems of a provider in a health network, and wherein developing the set of machine learning trained computer models comprises:
clustering patients on a projected feature space, based on outcome-differentiating features and weights, to generate a plurality of clusters, the clusters in the plurality of clusters being associated with corresponding behavioral phenotypes, to thereby generate subgroup level evidence data, wherein the behavioral phenotypes comprise characteristics of a cohort of patients who are similar in terms of interactional, contextual, and behavioral features driving differential patient engagement outcomes, and
executing supervised machine learning operations on computer models based on input patient features extracted from the one or more corpora of patient data to train regressors and estimators of the computer models and store corresponding trained computer model parameters for configuring the computer models to generate the set of machine learning trained computer models, wherein each machine learning trained computer model operates on the input patient features to predict whether a corresponding patient, based on the input patient features, will have a positive response to a corresponding targeted behavior;
match, by the personalized patient engagement engine, based on new patient input data for a given patient, the given patient to a behavioral phenotype of the behavioral phenotypes, wherein the plurality of behavioral phenotypes are composed of a number of prototypical patient cases according to their interactional, contextual, and behavioral features over the period of time;
executing, in the data processing system, the set of machine learning trained computer models on features extracted from the new patient input data to generate estimates of a propensity of positive behavioral responses of each of the plurality of targeted behaviors;
dynamically update, by the personalized patient engagement engine, personalized intervention effectiveness rankings based on what has been shown to lead to positive responses for individuals with a similar behavioral profile, based on a corresponding cluster in the plurality of clusters, the matched behavioral phenotype, and the generated estimates of the propensity of the positive behavioral responses;
generate, by the personalized patient engagement engine, an intervention recommendation for the given patient based on the personalized intervention effectiveness rankings relative to the patient given an assigned goal and an individual intervention effect estimation of achieving the assigned goal; and
provide, by the personalized patient engagement engine, the intervention recommendation to a care manager.

9. The computer program product of claim 8, wherein the computer readable program further causes the data processing to utilize at least one machine learning based causal inference pipeline to generate causal recommendations, and wherein the at least one machine learning based causal inference pipeline comprises engagement modeling or intervention effect estimation modeling.

10. The computer program product of claim 8, wherein developing the set of machine learning trained computer models comprises:
performing feature engineering on the anonymized unstructured care management notes to identify interactional features;
extracting context and patient behavior-related features from the anonymized unstructured care management notes; and
quantitatively identifying patient engagement based on the extracted context and patient behavior-related features to form patient engagement output.

11. The computer program product of claim 10, wherein developing the set of machine learning trained computer models further comprises:

performing feature engineering on the anonymized structured patient-care management records to identify interactional features;
extracting context and patient behavior-related features from the anonymized structured patient-care management records;
extracting engagement features from the patient engagement output; and
identifying patient behavioral responses to target behaviors.

12. The computer program product of claim 11, wherein matching the given patient to a behavioral phenotype comprises matching the given patient according to similarity of the given patient's interactional, contextual, and behavioral features to the prototypical cases of each behavioral phenotype.

13. The computer program product of claim 11, wherein the computer readable program causes the data processing to provide corrections and interpretations to the extracted engagement features.

14. The computer program product of claim 8, wherein the computer readable program causes the data processing to:
assign one or more tasks to the given patient based on the recommended intervention; and
store recommendation records for the recommended intervention to a database.

15. A data processing system comprising:
a processor; and
a memory coupled to the processor, wherein the memory has stored therein a computer readable program, wherein the computer readable program, when executed on the processor, causes the data processing system to implement a personalized patient engagement engine, wherein the computer readable program causes the data processing to:
develop, by the personalized patient engagement engine, a set of machine learning trained computer models that predict patient engagement to each of a plurality of targeted behaviors, wherein patient engagement is patient self-monitoring of lifestyle choices, goal adoption, and enlistment of self-efficacy beliefs, based on patient engagement semantics in one or more electronic corpora of patient data, comprising anonymized unstructured care management notes and anonymized structured patient-care management records, for a plurality of patients over a period of time, wherein the one or more corpora of patient data comprises patient data, for a population of patients, obtained from computing systems of a provider in a health network, and wherein developing the set of machine learning trained computer models comprises:
clustering patients on a projected feature space, based on outcome-differentiating features and weights, to generate a plurality of clusters, the clusters in the plurality of clusters being associated with corresponding behavioral phenotypes, to thereby generate subgroup level evidence data, wherein the behavioral phenotypes comprise characteristics of a cohort of patients who are similar in terms of interactional, contextual, and behavioral features driving differential patient engagement outcomes, and
executing supervised machine learning operations on computer models based on input patient features extracted from the one or more corpora of patient data to train regressors and estimators of the computer models and store corresponding trained computer model parameters for configuring the computer models to generate the set of machine learning trained computer models, wherein each machine learning trained computer model operates on the input patient features to predict whether a corresponding patient, based on the input patient features, will have a positive response to a corresponding targeted behavior;
match, by the personalized patient engagement engine, based on new patient input data for a given patient, the given patient to a behavioral phenotype of the behavioral phenotypes, wherein the plurality of behavioral phenotypes are composed of a number of prototypical patient cases according to their interactional, contextual, and behavioral features over the period of time;
executing, in the data processing system, the set of machine learning trained computer models on features extracted from the new patient input data to generate estimates of a propensity of positive behavioral responses of each of the plurality of targeted behaviors;
dynamically update, by the personalized patient engagement engine, personalized intervention effectiveness rankings based on what has been shown to lead to positive responses for individuals with a similar behavioral profile, based on a corresponding cluster in the plurality of clusters, the matched behavioral phenotype, and the generated estimates of the propensity of the positive behavioral responses;
generate, by the personalized patient engagement engine, an intervention recommendation for the given patient based on the personalized intervention effectiveness rankings relative to the patient given an assigned goal and an individual intervention effect estimation of achieving the assigned goal; and
provide, by the personalized patient engagement engine, the intervention recommendation to a care manager.

16. The data processing system of claim 15, wherein developing the set of machine learning trained computer models comprises:
performing feature engineering on the anonymized unstructured care management notes to identify interactional features;
extracting context and patient behavior-related features from the anonymized unstructured care management notes; and
quantitatively identifying patient engagement based on the extracted context and patient behavior-related features to form patient engagement output.

17. The data processing system of claim 16, wherein developing the set of machine learning trained computer models further comprises:
performing feature engineering on the anonymized structured patient-care management records to identify interactional features;
extracting context and patient behavior-related features from the anonymized structured patient-care management records;
extracting engagement features from the patient engagement output; and
identifying patient behavioral responses to target behaviors.

18. The data processing system of claim 17, wherein matching the given patient to a behavioral phenotype comprises matching the given patient according to similarity of the given patient's interactional, contextual, and behavioral features to the prototypical cases of each behavioral phenotype.

19. The data processing system of claim 17, further comprising providing corrections and interpretations to the extracted engagement features.

20. The data processing system of claim 15, wherein the computer readable program further causes the data processing system to utilize at least one machine learning based causal inference pipeline to generate causal recommendations, and wherein the at least one machine learning based causal inference pipeline comprises engagement modeling or intervention effect estimation modeling.

* * * * *